(12) United States Patent
Yoshimi et al.

(10) Patent No.: US 11,604,199 B2
(45) Date of Patent: Mar. 14, 2023

(54) TREATMENT LIQUID FOR EXCLUSION OF STEROID INCLUDED IN CYCLODEXTRIN

(71) Applicant: FUJIREBIO INC., Tokyo (JP)

(72) Inventors: Tatsunari Yoshimi, Tokyo (JP); Kyoko Teruyama, Tokyo (JP)

(73) Assignee: FUJIREBIO INC., Tokyo (JP)

( * ) Notice: Subject to any disclaimer, the term of this patent is extended or adjusted under 35 U.S.C. 154(b) by 0 days.

(21) Appl. No.: 16/765,018

(22) PCT Filed: Nov. 16, 2018

(86) PCT No.: PCT/JP2018/042415
§ 371 (c)(1),
(2) Date: May 18, 2020

(87) PCT Pub. No.: WO2019/098314
PCT Pub. Date: May 23, 2019

(65) Prior Publication Data
US 2020/0355705 A1    Nov. 12, 2020

(30) Foreign Application Priority Data
Nov. 17, 2017  (JP) .............................. JP2017-222240

(51) Int. Cl.
*G01N 33/74*  (2006.01)

(52) U.S. Cl.
CPC ....... *G01N 33/743* (2013.01); *G01N 2400/18* (2013.01)

(58) Field of Classification Search
CPC .... G01N 33/548; G01N 33/92; G01N 33/743; G01N 33/5436; G01N 33/5306; G01N 2496/25; G01N 2400/18
See application file for complete search history.

(56) References Cited

U.S. PATENT DOCUMENTS

| | | | |
|---|---|---|---|
| 4,956,274 | A | 9/1990 | Khanna et al. |
| 5,679,573 | A | 10/1997 | Williams et al. |
| 7,087,395 | B1 | 8/2006 | Garrity et al. |
| 2008/0194784 | A1 | 8/2008 | Choi et al. |

(Continued)

FOREIGN PATENT DOCUMENTS

| | | |
|---|---|---|
| JP | S64-85081 A | 3/1989 |
| JP | H04-326046 A | 11/1992 |
| JP | H11-510598 A | 9/1999 |

(Continued)

OTHER PUBLICATIONS

Souza, G. Liposomes Method and Protocols(second edition re-print of 2016 edition).Method in Molecular Biology: Springer Protocols. Humana Press (Year: 2017).*

(Continued)

*Primary Examiner* — Rebecca M Fritchman
(74) *Attorney, Agent, or Firm* — Oliff PLC (57) ABSTRACT

In a method for immunologically quantifying a steroid, it is possible to exclude a steroid from cyclodextrin when a standard solution containing the steroid included in cyclodextrin is treated with a surfactant, which thereby suppresses the deviation in behavior of the antigen-antibody reaction between the specimen (test sample) and the standard solution, and then significantly improves the accuracy of steroid quantification.

1 Claim, 7 Drawing Sheets

(56) References Cited

U.S. PATENT DOCUMENTS

2014/0113346 A1\* 4/2014 Ge .................... C02F 3/342
435/174

FOREIGN PATENT DOCUMENTS

| JP | 2005-503534 | A | 2/2005 |
|----|-------------|---|--------|
| JP | 2011-117779 | A | 6/2011 |
| JP | 2017-142241 | A | 8/2017 |
| WO | 97/05491 | A1 | 2/1997 |

OTHER PUBLICATIONS

Feb. 19, 2019 International Search Report issued in International Patent Application No. PCT/JP2018/042415.
Nov. 25, 2020 Search Report issued in European Patent Application No. 18878307.0.
Timothy W. Ryan. "ThermoFisher Scientific: Certificate of Analysis Product Name: Triton X-100 Surfact-Amps Detergent Solution, 50 ml". Aug. 28, 2012, pp. 1-1, URL: https://www.thermofisher.com/document-connect/document-connect.html?url=https%3A%2F%2Fassets.thermofisher.com%2FTFS-Assets%2FLSG%2Fcertificate%2FCertificates%2520of%2520Analysis%2FNH176397_85111.pdf&title=TkgxNzYz0Tc=>.
M. Cepeda et al. "Competition Between Surfactant Micellization and Complexation by Cyclodextrin". Organic & Biomolecular Chemistry, vol. 11, No. 7, Jan. 1, 2013, pp. 1093-1102.
May 19, 2020 International Preliminary Report on Patentability issued in International Patent Application No. PCT/JP2018/042415.

\* cited by examiner

TREATMENT LIQUID FOR EXCLUSION OF STEROID INCLUDED IN CYCLODEXTRIN

TECHNICAL FIELD

The present invention relates to a treatment liquid for use in exclusion of a steroid included in cyclodextrin, containing a surfactant as an active ingredient. The present invention also relates to the use of the treatment liquid in the immunological quantification of a steroid.

BACKGROUND ART

In the case of immunologically quantifying the target (antigen) contained in a specimen (test sample), it is common to measure the signal intensity of the antigen-antibody reaction in the specimen and the signal intensity of the antigen-antibody reaction in the standard solution containing the target at a predetermined concentration, and then compare the measured values. In order to perform this quantification with high accuracy, it is necessary to match the behaviors of the antigen-antibody reactions in the specimen and the standard solution as much as possible.

For example, although human serum is usually used as a specimen (test sample) in the case of immunologically quantifying a steroid, serum is often used as well in the preparation of a standard solution so that the behaviors of the antigen-antibody reactions in the specimen and the standard solution will not deviate. However, in the case of using a serum-based standard solution, it is impossible to eliminate a lot-to-lot difference and infection risk originating from the raw material.

For this reason, in the preparation of a standard solution, a buffer solution containing a protein such as bovine serum albumin is used instead of serum. In this case, however, the steroid contained in the standard solution exhibits a tendency to decompose with time, which causes a problem that its signal intensity decreases when measured. In addition, steroids, which are hydrophobic, are easily adsorbed to the container and the constituting ingredients of the standard solution, which also causes a decrease in signal intensity when measured.

Therefore, in order to suppress such a decrease in signal intensity, it has been proposed to add cyclodextrin to the standard solution, and to allow the hydrophobic interior of the cyclodextrin to include a steroid, achieving stabilization (PTL 1).

CITATION

Patent Literature

[PTL 1] International Publication No. WO1997/005491

SUMMARY OF INVENTION

Technical Problem

However, when the present inventors tried immunological quantification of a steroid contained in a specimen (test sample) using a standard solution containing the steroid included in cyclodextrin, it was found that the behaviors of the antigen-antibody reactions in the specimen and the standard solution were greatly different, which resultantly made it difficult to accurately quantify the steroid (see Example 1-1).

The present invention has been made in view of the above problem of the related art, and an object thereof is to improve the accuracy of steroid quantification in a method for immunologically quantifying a steroid using a standard solution containing the steroid included in cyclodextrin.

Solution to Problem

The present inventors have made earnest studies to solve the above problem, and have found as a result that it is possible to exclude a steroid from cyclodextrin when a standard solution containing the steroid included in cyclodextrin is treated with a surfactant.

This exclusion effect was particularly excellent in a surfactant having an acyl group or alkyl group having 8 carbon atoms and a surfactant having asteroid skeleton, and was observed for any of aldosterone, progesterone, 25-hydroxyvitamin D, and estradiol included in cyclodextrin. In addition, these surfactants exhibited excellent effects not only in the case of using a buffer solution-based standard solution but also in the case of using a serum-based standard solution.

Moreover, the present inventors have found that, in both non-competitive and competitive steroid immunoassay systems, the action of surfactant suppresses the deviation in behavior of the antigen-antibody reaction between the specimen (test sample) and the standard solution, and then significantly improves the accuracy of quantification. The above findings have completed the present invention.

Specifically, the present invention relates to the use of a surfactant for use in exclusion of a steroid included in cyclodextrin, and particularly to the use in the immunological quantification of a steroid. More specifically, the present invention provides the following.

[1] A treatment liquid for use in exclusion of a steroid included in cyclodextrin, comprising a surfactant as an active ingredient.

[2] The treatment liquid according to [1], wherein the surfactant has an acyl group or alkyl group having 8 carbon atoms, or has a steroid skeleton.

[3] The treatment liquid according to [2], wherein the surfactant is at least one selected from the group consisting of the following (a) to (e):
(a) surfactants having octanoyl groups and glucamine groups;
(b) surfactants having octyl groups and polyoxyethylene groups;
(c) surfactants having octyl groups, sulfonate groups, and ammonium groups;
(d) surfactants having steroid skeletons, sulfonate groups, and ammonium groups; and
(e) surfactants having steroid skeletons and carboxylate groups.

[4] The treatment liquid according to [3], wherein the surfactant is at least one selected from the group consisting of N-octanoyl-N-methylglucamine, poly(oxyethylene)octylphenyl ether, N-octyl-N,N-dimethyl-3-ammonio-1-propanesulfonate, 3-[(3-cholamidopropyl)dimethylammonio]-1-propanesulfonate, and sodium deoxycholate.

[5] The treatment liquid according to any one of [1] to [4], wherein the cyclodextrin is at least one selected from the group consisting of β-cyclodextrin, hydroxypropyl β-cyclodextrin, and γ-cyclodextrin.

[6] The treatment liquid according to any one of [1] to [5], wherein the steroid is at least one selected from the group consisting of aldosterone, progesterone, 25-hydroxyvitamin D, and estradiol.

[7] The treatment liquid according to any one of [1] to [6] for use to exclude a steroid included in cyclodextrin in a standard solution for steroid immunological quantification containing the steroid and the cyclodextrin.

[8] A method for immunologically quantifying a steroid, comprising:
reacting an anti-steroid antibody with each of a test sample and a standard solution containing a steroid and cyclodextrin;
measuring signal intensities of antigen-antibody reactions in the test sample and the standard solution; and
comparing the signal intensity in the test sample with the signal intensity in the standard solution, wherein
the treatment liquid according to [7] is added to a reaction system of the antigen-antibody reaction in the standard solution.

[9] A kit for immunologically quantifying a steroid, comprising at least the following (a) to (c):
(a) an anti-steroid antibody;
(b) a standard solution containing a steroid and cyclodextrin; and
(c) the treatment liquid according to [7].

Advantageous Effects of Invention

The present invention made it possible to suppress the behavioral deviation between the specimen (test sample) and the standard solution by allowing coexistence of a surfactant during the antigen-antibody reaction in the steroid immunoassay system. This made it possible to quantify a steroid with high accuracy not only in the case of using a serum-based standard solution but also in the case of using a buffer solution-based standard solution (for example, a serum-free and protein-free standard solution).

DESCRIPTION OF EMBODIMENTS

The present invention provides a treatment liquid for use in exclusion of a steroid included in cyclodextrin, containing a surfactant as an active ingredient.

In the present invention, "inclusion" means that cyclodextrin incorporates a molecule into its cyclic structure, and "exclusion" means that a molecule included in cyclodextrin is desorbed from cyclodextrin.

The "cyclodextrin" in the present invention is a cyclic oligosaccharide in which a plurality of glucoses is bonded to form a cyclic structure. The cyclodextrin applied to the present invention is not particularly limited as long as it has a steroid inclusion action, and examples thereof include α-cyclodextrin, β-cyclodextrin, hydroxypropyl β-cyclodextrin, and γ-cyclodextrin. Among these, β-cyclodextrin, hydroxypropyl β-cyclodextrin, and γ-cyclodextrin are preferable, and hydroxypropyl β-cyclodextrin is particularly preferable.

The "steroid" in the present invention is a general term for compounds having a steroid skeleton (cyclopentanohydrophenanthrene skeleton). Examples of the steroid include steroid hormones and derivatives thereof which retain a steroid skeleton (for example, synthetic steroids such as anabolic steroids, antiandrogens, and anti-follicular hormone agents). Examples of the steroid hormones include male hormones, follicular hormones, luteinizing hormones (for example, progesterone), and corticoids (for example, glucocorticoids and mineralocorticoids). The steroid applied to the present invention is not particularly limited as long as it is included in cyclodextrin. For example, aldosterone, progesterone, 25-hydroxyvitaminD, and estradiol are preferable.

Aldosterone is a type of steroid hormone secreted from the zona glomerulosa of the adrenal cortex (mineralocorticoid), and promotes sodium ion reabsorption and associated water absorption primarily in the renal tubules, and the excretion of potassium ions and hydrogen ions in exchange for sodium ions.

Progesterone is a type of steroid hormone synthesized in the corpus luteum of the ovary (luteinizing hormone) and has effects such as changes in secretory phase of the endometrium, maintenance of pregnancy, increased body temperature, ovulation suppression, and mammary gland development.

25-Hydroxyvitamin D is a hormone precursor created by hydroxylating vitamin D in the liver, and is involved in maintaining bone and mineral metabolism.

Estradiol is a type of steroid hormone (follicular hormone) created in granulosa cells of the ovary, cells of the theca externa, placenta, adrenal cortex, and testicular stromal cells, and has effects such as promotion of mammary glandular cell proliferation, ovarian ovulation control, lipid metabolism control, insulin action, blood coagulation action, central nerve (consciousness) feminization, skin thinning, and arteriosclerosis inhibition by LDL decrease and VLDL.HDL increase.

In the treatment liquid of the present invention, a surfactant is used to exclude the included steroid from the cyclodextrin. The "surfactant" in the present invention is a compound which lowers the surface tension in an aqueous solution, and has a hydrophilic moiety and a hydrophobic moiety in the molecule. The surfactant applied to the present invention is not particularly limited as long as it has such an exclusion action, and is preferably at least one selected from the group consisting of a surfactant having an acyl group or alkyl group having 8 carbon atoms and a surfactant having a steroid skeleton, and more preferably any one selected from the group.

The surfactant having an acyl group having 8 carbon atoms is preferably one having a hydrophobic octanoyl group (C8 (having 8 carbon atoms; hereinafter the same)) and a hydrophilic glucamine group. Examples thereof include, but are not limited to, N-octanoyl-N-methylglucamine (nonionic, MEGA8 (manufactured by Dojindo Laboratories) and the like). The surfactant having an alkyl group having 8 carbon atoms is preferably one having a hydrophobic octyl group (C8) and a hydrophilic poly(oxyethylene) group. Examples thereof include, but are not limited to, poly(oxyethylene)octylphenyl ether (nonionic, Triton X (such as Triton X705 and Triton X100 (manufactured by Nacalai Tesque, Inc.)) and the like). An additional surfactant having an alkyl group having 8 carbon atoms is preferably one having a hydrophobic octyl group (C8) and a hydrophilic moiety containing a sulfonate group and an ammonium group. Examples thereof include, but are not limited to, N-octyl-N,N-dimethyl-3-ammonio-1-propanesulfonate (amphoteric, CHAPS (manufactured by Tokyo Chemical Industry Co., Ltd.) and the like). In addition, the surfactant having a steroid skeleton is preferably one having a hydrophobic steroid skeleton and a hydrophilic moiety containing a sulfonate group and an ammonium group, and one having a hydrophobic steroid skeleton and a hydrophilic moiety containing a carboxylate group. Examples thereof include, but are not limited to, 3-[(3-cholamidopropyl)dimethylammonio]-1-propanesulfon ate (amphoteric, CHAPS (manufactured by Dojindo Laboratories) and the like) and sodium deoxycholate (anionic).

Among these, N-octanoyl-N-methylglucamine (such as MEGA8) having a hydrophobic octanoyl group (C8) and a hydrophilic glucamine group, and 3-[(3-cholamidopropyl) dimethylammonio]-1-propanesulfon ate (such as CHAPS) are particularly preferable because they exhibit an excellent exclusion effect regardless of the type of steroid or immunoassay, and N-octanoyl-N-methylglucamine is particularly preferable.

The concentration of the surfactant contained in the treatment liquid of the present invention is not particularly limited as long as it can bring about an exclusion action on the steroid when added to a reaction system containing the steroid included in cyclodextrin. The concentration of the surfactant in the treatment liquid can be appropriately adjusted so that the concentration after the treatment liquid is added to the reaction system is usually 0.005 to 5% and preferably 0.01 to 2%. For example, if the addition to the reaction system is intended for n-fold dilution, it suffices to prepare a treatment liquid containing a surfactant having an n-fold concentration in advance.

The treatment liquid of the present invention can be prepared based on, for example, a buffer solution. The buffer solution is not particularly limited, and examples thereof include GOOD buffer solution (such as HEPES and MOPS), tris buffer solution (such as Tris HCl buffer solution, TE buffer solution, TAE buffer solution, TBE buffer solution, and tris buffered saline), and phosphate buffer solution (such as phosphate buffered saline). The pH value of the buffer solution is usually 5.0 to 9.0 and preferably 6.0 to 8.0.

The treatment liquid of the present invention can also be prepared based on serum. The serum is not particularly limited, and examples thereof include animal-derived serum (serum derived from animals such as humans, cows, horses, sheep, goats, pigs, llamas, dogs, chickens, donkeys, cats, rabbits, guinea pigs, hamsters, rats, and mice) and defatted serum (such as DDC Mass Spect Gold (manufactured by VERITAS Corporation)).

The treatment liquid of the present invention may contain as necessary a salt concentration adjusting molecule such as sodium chloride and a preservative (antiseptic) such as sodium azide. Also, it may contain, for example, a protein component such as bovine serum albumin (BSA), a blocking agent, a protein stabilizer, a sensitizer, a saccharide, a hydrophilic polymer (for example, polyethylene glycol and polyvinyl alcohol), and the like.

The treatment liquid of the present invention can be used to exclude a steroid from the steroid included in cyclodextrin, which is present in a standard solution for use in a method for immunologically quantifying a steroid. The method for immunologically quantifying a steroid generally includes (the steps of) reacting an anti-steroid antibody with each of a test sample and a standard solution; measuring signal intensities of antigen-antibody reactions in the test sample and the standard solution; and comparing the signal intensity in the test sample with the signal intensity in the standard solution.

Here, consider the case where an antibody is added to carry out an antigen-antibody reaction in a state where the steroid in the standard solution is included in cyclodextrin. Then, compared with the case where an antigen-antibody reaction is carried out on a test sample containing a free steroid, the free steroid concentration in the reaction system differs. Therefore, there is a deviation in the number of antigen molecules bound to the antibody. However, in the method for immunologically quantifying a steroid of the present invention, the treatment liquid of the present invention is added to the reaction system to exclude the steroid from the cyclodextrin, which thereby makes it possible to suppress the occurrence of a deviation in the number of antigen molecules bound to such an antibody.

The "test sample" used in the method for immunologically quantifying a steroid of the present invention is not particularly limited as long as it is a sample in which steroid can be present. A blood specimen is generally used for the purpose of measuring a steroid concentration, which is the basis for diagnosis of a disease associated with a steroid abnormality. The blood specimen is preferably serum or plasma. In addition, the test sample maybe diluted with a buffer solution or serum, may be added with cyclodextrin mainly for the purpose of stabilizing the steroid, and may be added with the treatment liquid of the present invention as described later. Examples of the buffer solution and the serum include ones similar to those given as the bases of the treatment liquid.

The "standard solution" used in the method for immunologically quantifying a steroid of the present invention is not particularly limited as long as it contains predetermined concentrations of steroid and the cyclodextrin, and may be buffer solution-based or serum-based. Examples of the buffer solution and serum serving as the bases include ones similar to those mentioned as the bases of the treatment liquid. Buffer solution-based ones may or may not contain a protein component such as bovine serum albumin.

In the method for immunologically quantifying a steroid of the present invention, examples of the method for immunologically measuring a steroid include, but are not limited to, CLEIA (chemiluminescence enzyme immunoassay) or EIA (enzyme immunoassay) using an enzyme as a label (labeling substance); RIA (radioimmunoassay) using a radioisotope as a label; CLIA (chemiluminescence immunoassay) using a chemiluminescent compound as a label; latex agglomeration; and immunological techniques such as immunochromatography. These immunological measurements maybe non-competitive measurement methods or competitive measurement methods.

The antibody used in the immunological technique may be of any isotype such as IgG, IgM, IgA, IgD, IgE, and IgY. Such antibodies can also be polyclonal or monoclonal antibodies (for example, chimeric antibodies, humanized antibodies, human antibodies) or antibody fragments thereof. Examples of the antibody fragments include, but are not limited to, F(ab')2, Fab', Fab, Fv, single chain antibodies, and diabodies. The antibody is preferably a monoclonal antibody. As the monoclonal antibody, it is possible to use one prepared by a known method such as a hybridoma method or a recombinant DNA method.

As an anti-steroid antibody used in the above-described method for immunologically measuring a steroid, it is possible to use an antibody bound with a labeling substance. The labeling substance is not particularly limited as long as it can be detected when bound to an antibody, and examples thereof include enzymes such as alkaline phosphatase (ALP), horseradish peroxidase (HRP), and (β-galactosidase (β-gal); fluorescent dyes such as fluorescein isothiocyanate (FITC) and rhodamineisothiocyanate (RITC); radioisotopes such as $^{125}$I; fluorescent proteins such as allophycocyanin (APC) and phycoerythrin (R-PE); avidin; biotin; latex; and gold particles.

In the case of using an enzyme as the labeling substance, a chromogenic substrate, a fluorescent substrate, a chemiluminescent substrate, or the like can be added as the substrate to perform various detections depending on the substrate.

As the above-described method for immunologically measuring a steroid, in addition to the above-described method for directly detecting a steroid using an anti-steroid antibody bound with a labeling substance, it is also possible to use a method for indirect detection using, for example, a secondary antibody bound with the labeling substance instead of binding the labeling substance to the anti-steroid antibody. Here, the "secondary antibody" is an antibody which exhibits reactivity with an anti-steroid antibody. For example, when the anti-steroid antibody is prepared as a mouse antibody, an anti-mouse IgG antibody can be used as the secondary antibody. As the secondary antibody, label secondary antibodies are commercially available which can be used to label antibodies derived from various biological species such as rabbits, goats, and mice. An appropriate secondary antibody can be selected and used depending on the species from which the anti-steroid antibody is derived. In addition, instead of the secondary antibody, protein G or protein A bound with the labeling substance can be used.

For binding between the anti-steroid antibody and the labeling substance or between the secondary antibody and the labeling substance, a conventionally known method can be appropriately employed. In addition, for such binding, a biotin-avidin system can be used. For example, this method biotinylates an anti-steroid antibody, allows an avidinylated labeling substance to act on the biotinylated anti-steroid antibody, and use the interaction between biotin and avidin to bind the labeling substance to the anti-steroid antibody.

As the detection principle of the immunological technique, the sandwich method and the competitive method are suitable. The sandwich method captures a detection target substance (for example, an antigen (steroid)) with a capture antibody (for example, an anti-steroid antibody) immobilized (coated) on a solid phase, and allows a detection antibody bound with a labeling substance (for example, a secondary antibody bound with a labeling substance) to recognize the captured detection target substance, to thereby perform detection depending on the type of the labeling substance. As the solid phase, it is possible to use, for example, fine particles such as magnetic particles and latex particles, plates such as plastic plates, or fibrous substances such as nitrocellulose.

The capture antibody may be immobilized directly, but may be immobilized indirectly, on the solid phase. For example, the capture antibody can be indirectly immobilized on the solid phase by immobilizing a substance bindable to the capture antibody on the solid phase and binding the capture antibody to the substance. Examples of the substance bindable to the capture antibody include, but are not limited to, the above-described secondary antibody, protein G, and protein A. For immobilization to the solid phase, a conventionally known method can be appropriately employed. In addition, in the case where the capture antibody is biotinylated, an avidinylated solid phase can be used.

Consider the case of using, in the sandwich method, a standard solution containing asteroid (detection target substance) and cyclodextrin. Then, the following procedure is preferable. Specifically, for example, the standard solution, the treatment liquid of the present invention, and the coated capture antibody are mixed to carry out a first antigen-antibody reaction (first reaction), thereby forming a complex (immunocomplex) of the steroid and the capture antibody. After separating and washing this immunocomplex, a detection antibody bound with the labeling substance is added thereto to carry out a second antigen-antibody reaction (second reaction). Thereby, various detections are performed depending on the labeling substance.

As the detection antibody, it is possible to use not only an antibody bindable only to a steroid but also an antibody specifically bindable to a complex of a steroid and an antibody. Therefore, the "anti-steroid antibody" in the present invention includes both of these antibodies.

Suitable as the sandwich method are, for example, the sandwich CLIA as a form of the CLIA, the sandwich CLEIA as a form of the CLEIA, and the IRMA (immunoradiometric assay) as a form of the RIA.

Meanwhile, for example, a first embodiment of the competitive method allows the coated detection target substance and the detection target substance in the sample to compete with each other for binding to the detection antibody bound with the labeling substance. Consider the case of using a standard solution containing a steroid (detection target substance) and cyclodextrin. For example, the standard solution, the treatment liquid of the present invention, and the detection antibody bound with the labeling substance are mixed to carry out a first antigen-antibody reaction (first reaction). The coated detection target substance is added thereto to carry out a second antigen-antibody reaction (second reaction).

In addition, for example, a second embodiment of the competitive method allows the detection target substance in the sample and the detection target substance bound with the labeling substance to compete with each other for binding to the coated capture antibody. Consider the case of using a standard solution containing a steroid (detection target substance) and cyclodextrin. For example, the standard solution, the treatment liquid of the present invention, and the detection target substance bound with the labeling substance are mixed, and the coated capture antibody is added thereto to carry out an antigen-antibody reaction.

A conventionally known method can be appropriately employed to immobilize the detection target substance and the capture antibody on the solid phase in the competitive method, and such immobilization may be direct as described above, or may be indirect.

In the method for immunologically quantifying a steroid of the present invention, the treatment liquid of the present invention may be added not only to the standard solution but also to the test sample. Since the treatment liquid of the present invention contains a surfactant, its addition to the test sample in the same manner achieves the same surfactant concentration as that of the standard solution, thereby making it possible to carry out an antigen-antibody reaction under more approximate conditions. In addition, the treatment liquid of the present invention is added to the reaction system of the antigen-antibody reaction between the detection target substance and its antibody so that the concentration of the surfactant is the above desired concentration. For example, the treatment liquid may be added in advance to another solution used in reaction system (a detection antibody bound with the labeling substance in the first embodiment of the competition method, a detection target substance bound with the labeling substance in the second embodiment of the competition method, and the like), or their solution may be added in advance with the surfactant to serve as the treatment liquid of the present invention.

The quantification of the steroid concentration from the measured value obtained in the test sample is generally performed by comparison with the measured values of standard solutions containing steroid at various concentrations. In this case, the steroid concentration in the sample can be obtained by, for example, examining at which position on the standard curve created based on the measured values of the standard solutions the measured value obtained in the test sample is positioned.

The method for immunologically quantifying a steroid of the present invention can be used for diagnosis of diseases associated with abnormality in secretion volume of steroid hormones (evaluation of morbidity and risk thereof). Here, the "diseases associated with abnormality in secretion volume of steroid hormones" mean both diseases resulting from abnormality in secretion volume of steroid hormones and diseases with abnormal secretion volume of steroid hormones as a result of the development of the diseases. For example, it is known that the aldosterone concentration in the blood exhibits a high value in primary aldosteronism, renovascular hypertension, malignant hypertension, renin-producing tumor, Bartter syndrome, edematous disease (cirrhosis.heart failure), and the like, whereas the aldosterone concentration in the blood exhibits a low value in Addison disease, 21-hydroxylase deficiency, selective hypoaldosteronism, and the like. In addition, it is known that progesterone concentration in the blood exhibits a high value in congenital adrenal hyperplasia, Cushing's syndrome, adrenal tumor, and the like, and exhibits a low value in ovarian dysfunction, luteal insufficiency, and the like. Moreover, it is known that the concentration of 25-hydroxyvitamin D in the blood exhibits a high value in vitamin D poisoning and the like, and exhibits a low value in rickets, osteomalacia, osteoporosis, and the like. In addition, it is known that the estradiol concentration in the blood exhibits a high value in hepatic disease, estrogen-producing tumor, congenital adrenocortical hyperplasia, multiple pregnancy, ovarian hyperstimulation syndrome, and the like, and exhibits a low value in ovarian dysfunction, premature ovarian failure, hypogonadotropism, Chiari-Frommel syndrome, and the like.

The present invention also provides a kit for immunologically quantifying a steroid which can be used in the above-described method for immunologically quantifying a steroid of the present invention. The kit of the present invention at least includes an anti-steroid antibody (antibody standard sample), a standard solution containing a steroid and cyclodextrin (standard steroid reagent), and the treatment liquid of the present invention. The kit can further be combined with a comparison reagent, a washing solution, a diluent, a dilution cartridge, and the like. In addition, in the case of using an enzyme label as the labeling substance, a substrate necessary for detecting the label, a reaction stop solution, and the like can be included.

In the case of using the above-described sandwich method as the detection principle, a coated steroid capture antibody or a solid phase immobilized with a substance bindable to the steroid capture antibody can be included, for example. Meanwhile, in the case of using the above-described competitive method as the detection principle, in addition to these solid phases, a coated detection target substance or a solid phase immobilized with a substance bindable to a detection target substance can be included, for example.

In addition, in the case where a primary antibody (an antibody directly bindable to an antigen) or a secondary antibody is not labeled, one labeled with a substance bindable to these antibodies can be included in the kit, for example. In addition, when the anti-steroid antibody is biotinylated, an avidinylated labeling substance can be included in the kit, for example. The kit of the present invention may further contain an instruction manual for using the kit.

The kit of the present invention can be used not only for research purposes but also as, for example, an in vitro diagnostic drug for the quantification of steroid concentration, which is a basis for diagnosis of diseases associated with the above-described abnormality in secretion volume of steroid hormones.

EXAMPLES

Hereinafter, the present invention is described in more detail based on Examples, but the present invention is not limited to the following examples. Note that, in each composition of the following examples, "%" means "% by weight."

Example 1

[Example 1-1] Verification of Inclusion Effect of Cyclodextrin on Aldosterone

In the present example, aldosterone was used as the antigen, and a buffer solution-based one was used as the standard solution. Specifically, first, aldosterone was added to each of the diluents added with 0%, 1%, and 3% concentrations of cyclodextrin (α-cyclodextrin (αCD), β-cyclodextrin (βCD), hydroxypropyl β-cyclodextrin (HPβCD), and γ-cyclodextrin (γCD)) to prepare an approximately 500 pg/mL aldosterone solution (standard solution). The compositions of the diluent were "50 mM MOPS (pH 7.2), 150 mM NaCl, 0.1% NaN$_3$."

Measurement was carried out for each aldosterone solution by the two-step method using anti-aldosterone antibody-binding particles (anti-aldosterone antibody-binding magnetic particles (antibody-binding particles) prepared by the conventional method) and an alkaline phosphatase-labeled anti-aldosterone immunocomplex antibody (alkaline phosphatase-labeled anti-aldosterone antibody (enzyme-labeled antibody) prepared by the conventional method). Specifically, the following steps (a) to (f) were carried out.
(a) About 30 μL of the sample (the aldosterone solution described above) is added to about 50 μL of the antibody-binding particles, and the mixture is stirred and reacted at 37° C. for 8 minutes (first reaction).
(b) B/F separation is carried out using a magnetic separator, followed by washing.
(c) About 50 μL of enzyme-labeled antibody is added, and the mixture is stirred and reacted at 37° C. for 8 minutes (second reaction).
(d) B/F separation is carried out using a magnetic separator, followed by washing.
(e) About 200 μL of AMPPD (substrate, 3-(2'-spiroadamantane)-4-methoxy-4-(3"-phosphoryloxy) phenyl-1,2-dioxetane.disodium salt) is added, and the mixture is stirred and reacted at 37° C. for 4 minutes (enzymatic reaction).
(f) The luminescence intensity of light having a maximum emission peak in the vicinity of a wavelength of 463 nm, which is emitted with the decomposition of the substrate, is measured.

Figure 1:
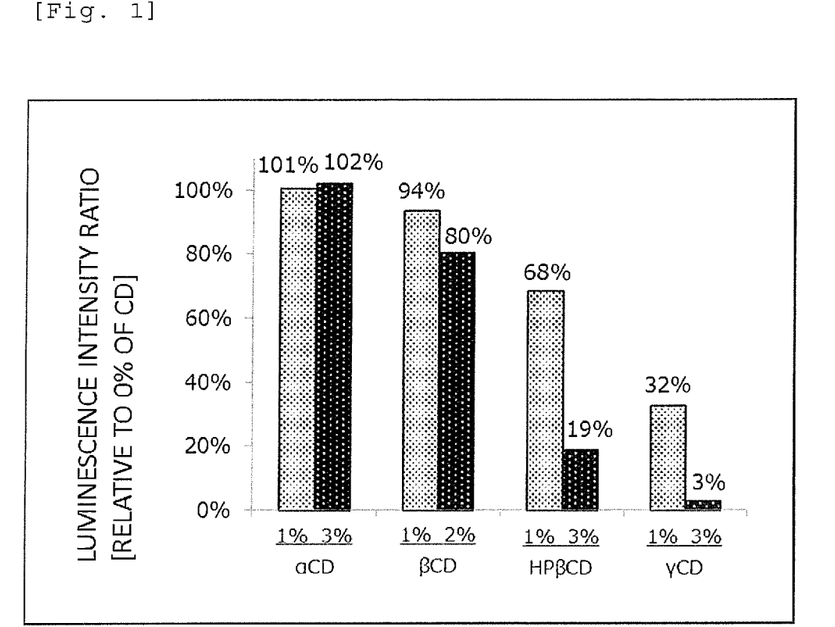
FIG. 1 is a graph illustrating the results of verifying the inclusion effect of cyclodextrin on aldosterone. As the cyclodextrin, α-cyclodextrin (αCD), β-cyclodextrin (βCD), hydroxypropyl β-cyclodextrin (HPβCD), and γ-cyclodextrin (γCD) were used.

FIG. 1 illustrates the ratio of luminescence intensity when the aldosterone solution with 1% or 3% concentration of cyclodextrin was used (luminescence intensity ratio [relative to 0% of CD]), where the luminescence intensity in the case of using the aldosterone solution with 0% concentration of cyclodextrin (0% CD) was set to 100%. As a result, the luminescence intensity was not substantially changed by the addition of αCD, but the luminescence intensity was reduced by the addition of other cyclodextrins (βCD, HPβCD, γCD). Therefore, aldosterone was conceivably included (FIG. 1). Since the rate of reduction in the luminescence intensity differed at the same concentration depending on the type of cyclodextrin, the inclusion action was conceivably strong in the order of αCD<βCD<HPβCD<γCD.

[Example 1-2] Verification of Stabilizing Effect of HPβCD on Aldosterone

In the present example, aldosterone was used as the antigen, and a buffer solution-based one was used as the standard solution. Specifically, first, aldosterone was added to each of the diluents added with 0.1% and 1% concentrations of HPβCD to prepare an approximately 300 pg/mL aldosterone solution (standard solution). The compositions of the diluent were "100 mM HEPES (pH 7.5), 150 mM NaCl, 0.5% BSA, 0.1% NaN$_3$."

The aldosterone solutions obtained (approximately 300 pg/mL aldosterone solutions) were stored at −80° C., 4° C., 25° C., and 37° C. for 45 days, and then subjected to measurement. Measurement was carried out for each aldosterone solution after storage by the two-step method using anti-aldosterone antibody-binding particles (anti-aldosterone antibody-binding magnetic particles (antibody-binding particles) prepared by the conventional method) and an alkaline phosphatase-labeled anti-aldosterone immunocomplex antibody (alkaline phosphatase-labeled anti-aldosterone antibody (enzyme-labeled antibody) prepared by the conventional method). Specifically, the following steps (a) to (f) were carried out.
(a) About 40 μL of the sample (the aldosterone solution described above) is added to about 250 μL of the antibody-binding particles, and the mixture is stirred and reacted at 37° C. for 10 minutes (first reaction).
(b) B/F separation is carried out using a magnetic separator, followed by washing.
(c) About 250 μL of enzyme-labeled antibody is added, and the mixture is stirred and reacted at 37° C. for 10 minutes (second reaction).
(d) B/F separation is carried out using a magnetic separator, followed by washing.
(e) About 200 μL of AMPPD (substrate, 3-(2'-spiroadamantane)-4-methoxy-4-(3"-phosphoryloxy) phenyl-1,2-dioxetane.disodium salt) is added, and the mixture is stirred and reacted at 37° C. for 5 minutes (enzymatic reaction).
(f) The luminescence intensity of light having a maximum emission peak in the vicinity of a wavelength of 447 nm, which is emitted with the decomposition of the substrate, is measured.

Figure 2:
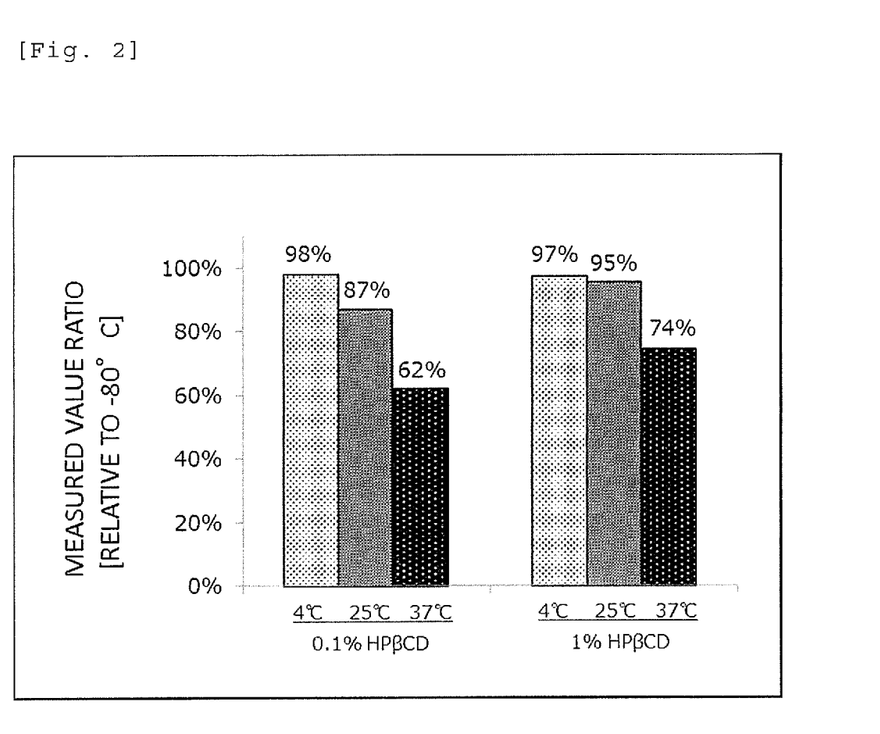
FIG. 2 is a graph illustrating the results of verifying the stabilizing effect of HPβCD on aldosterone.

FIG. 2 illustrates the ratio of luminescence intensity when the aldosterone solutions after storage for 45 days at 4° C., 25° C. and 37° C. were used (luminescence intensity ratio (measured value ratio) [relative to −80° C.]), where the luminescence intensity in the case of using the aldosterone solution after storage for 45 days at −80° C. was set to 100%. As a result, the higher the HPβCD concentration, the smaller the variation in the measured value when the temperature load was applied. Thus, HPβCD was considered to contribute to the stability of the standard solution (FIG. 2).

[Example 1-3] Effect of Excluding Aldosterone from HPβCD-1

In the present example, aldosterone was used as the antigen, and a buffer solution-based one was used as the standard solution. Specifically, first, aldosterone was added to the following standard solution diluent (with HPβCD) to prepare an approximately 1600 pg/mL aldosterone solution (1600 pg/mL CD (+) standard solution). Meanwhile, the following delipidated serum was used as a pseudo test sample diluent, and aldosterone was added thereto to prepare an approximately 1600 pg/mL aldosterone solution (1600 pg/mL specimen (pseudo test sample)). The standard solution diluents (with HPβCD) used were "50 mM MOPS (pH 7.2), 150 mM NaCl, 1% HPβCD, 0.1% NaN$_3$" and the delipidated serum used was "DDC Mass Spect Gold (serum free of steroidal hormones and cholesterol/TG, manufactured by VERITAS Corporation)."

In addition, the following treatment liquid base composition was used to prepare treatment liquids each of which was added or not added with twelve types of surfactants [sodium deoxycholate (manufactured by FUJIFILM Wako Pure Chemical Corporation), NLS (manufactured by Nacalai Tesque, Inc.), C12TAB (manufactured by Tokyo Chemical Industry Co., Ltd.), C2APS (manufactured by Tokyo Chemical Industry Co., Ltd.), C8APS (manufactured by Tokyo Chemical Industry Co., Ltd.), C12APS (manufactured by Tokyo Chemical Industry Co., Ltd.), CHAPS (manufactured by Dojindo Laboratories), Tween 20 (manufactured by FUJIFILM Wako Pure Chemical Corporation), Tween 80 (manufactured by FUJIFILM Wako Pure Chemical Corporation), Triton X100 (manufactured by Nacalai Tesque, Inc.), Triton X705 (manufactured by Sigma-Aldrich), and MEGA8 (manufactured by Dojindo Laboratories)]. The treatment liquid base compositions were "20 mM MOPS (pH 7.2), 300 mM NaCl, 0.1% $NaN_3$." The concentration of the surfactant in each treatment liquid was 1.2% for sodium deoxycholate and 2% for the others.

Measurement was carried out for each sample (1600 pg/mL CD (+) standard solution or 1600 pg/mL specimen) by the special two-step method using anti-aldosterone antibody-binding particles (anti-aldosterone antibody-binding magnetic particles (antibody-binding particles) prepared by the conventional method), an alkaline phosphatase-labeled anti-aldosterone immunocomplex antibody (alkaline phosphatase-labeled anti-aldosterone antibody (enzyme-labeled antibody) prepared by the conventional method), and each of the above treatment liquids. Specifically, the following steps (a) to (f) were carried out.

(a) About 30 μL of the sample is added to about 50 μL of the antibody-binding particles and about 20 μL of the treatment liquid, and the mixture is stirred and reacted at 37° C. for 8 minutes (first reaction).
(b) B/F separation is carried out using a magnetic separator, followed by washing.
(c) About 50 μL of enzyme-labeled antibody is added, and the mixture is stirred and reacted at 37° C. for 8 minutes (second reaction).
(d) B/F separation is carried out using a magnetic separator, followed by washing.
(e) About 200 μL of AMPPD (substrate, 3-(2'-spiroadamantane)-4-methoxy-4-(3''-phosphoryloxy) phenyl-1,2-dioxetane.disodium salt) is added, and the mixture is stirred and reacted at 37° C. for 4 minutes (enzymatic reaction).
(f) The luminescence intensity of light having a maximum emission peak in the vicinity of a wavelength of 463 nm, which is emitted with the decomposition of the substrate, is measured.

Figure 3:
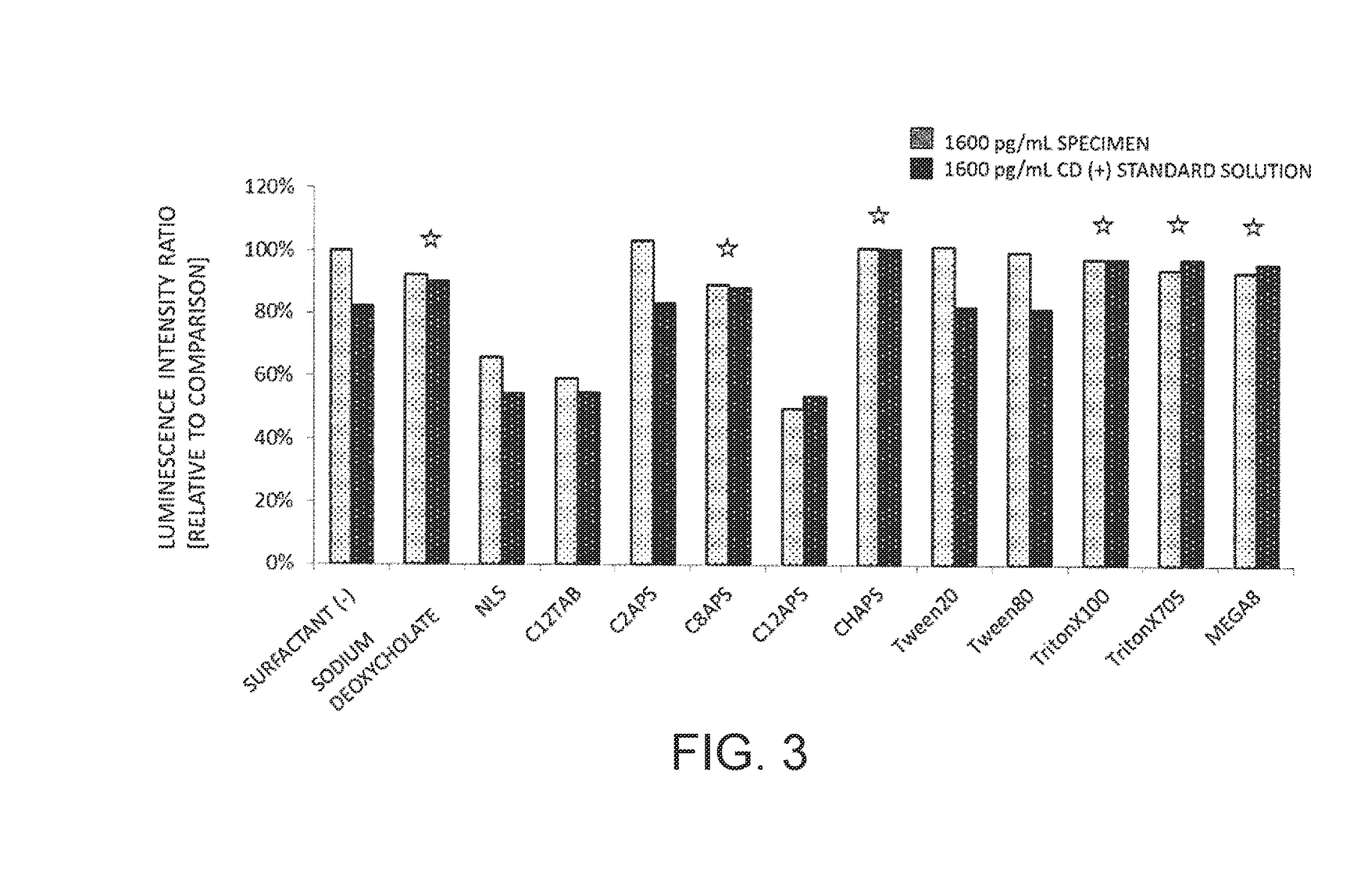
FIG. 3 is a graph illustrating the exclusion effect of various surfactants on aldosterone included in HPβCD. Measurement was performed by a non-competitive method (two-step method) using a buffer solution-based standard solution.

FIG. 3 illustrates the ratio of luminescence intensity when each treatment liquid was used and the 1600 pg/mL CD (+) standard solution or 1600 pg/mL specimen was used as the sample (luminescence intensity ratio [relative to comparison]), where the luminescence intensity in the case of using, as the treatment liquid, the treatment liquid not added with a surfactant (surfactant (−)) and using, as the sample, the 1600 pg/mL specimen was set to 100% (comparison). As a result, it was found that the surfactants having an exclusion effect (effect of increasing the reactivity of the 1600 pg/mL CD (+) standard solution without changing the reactivity of the 1600 pg/mL specimen) were sodium deoxycholate and CHAPS having a steroid skeleton, Triton X100, Triton X705, and C8APS having an alkyl group having 8 carbon atoms, and MEGA8 having an acyl group having 8 carbon atoms (star marks in FIG. 3).

[Example 1-4] Effect of Excluding Aldosterone from HPβCD-2

In the present example, aldosterone was used as the antigen, and a serum-based one was used as the standard solution. Specifically, first, aldosterone was added to a −HPβCD delipidated serum (DDC Mass Spect Gold) to prepare an approximately 2000 pg/mL aldosterone solution (2000 pg/mL specimen (pseudo test sample)). Meanwhile, aldosterone was added to a +HPβCD delipidated serum (the −HPβCD delipidated serum added with HPβCD to a 1% concentration) to prepare an approximately 2000 pg/mL aldosterone solution (2000 pg/mL CD (+) standard solution).

In addition, the following treatment liquid base composition was used to prepare treatment liquids each of which was added or not added with 5 types among the surfactants used in Example 1-3 (C12APS, CHAPS, Tween 20, Triton X705, MEGA8). The treatment liquid base compositions were "20 mM MOPS (pH 7.2), 300 mM NaCl, 0.1% $NaN_3$." The concentration of the surfactant in each treatment liquid was 3%.

Measurement was carried out for each sample (2000 pg/mL CD (+) standard solution or 2000 pg/mL specimen) by the special two-step method using anti-aldosterone antibody-binding particles (anti-aldosterone antibody-binding magnetic particles (antibody-binding particles) prepared by the conventional method), an alkaline phosphatase-labeled anti-aldosterone immunocomplex antibody (alkaline phosphatase-labeled anti-aldosterone antibody (enzyme-labeled antibody) prepared by the conventional method), and each of the above treatment liquids. Specifically, the following steps (a) to (f) were carried out.

(a) About 30 μL of the sample is added to about 50 μL of the antibody-binding particles and about 30 μL of the treatment liquid, and the mixture is stirred and reacted at 37° C. for 8 minutes (first reaction).
(b) B/F separation is carried out using a magnetic separator, followed by washing.
(c) About 50 μL of enzyme-labeled antibody is added, and the mixture is stirred and reacted at 37° C. for 8 minutes (second reaction).
(d) B/F separation is carried out using a magnetic separator, followed by washing.
(e) About 200 μL of AMPPD (substrate, 3-(2'-spiroadamantane)-4-methoxy-4-(3''-phosphoryloxy) phenyl-1,2-dioxetane.disodium salt) is added, and the mixture is stirred and reacted at 37° C. for 4 minutes (enzymatic reaction).
(f) The luminescence intensity of light having a maximum emission peak in the vicinity of a wavelength of 463 nm, which is emitted with the decomposition of the substrate, is measured.

Figure 4:
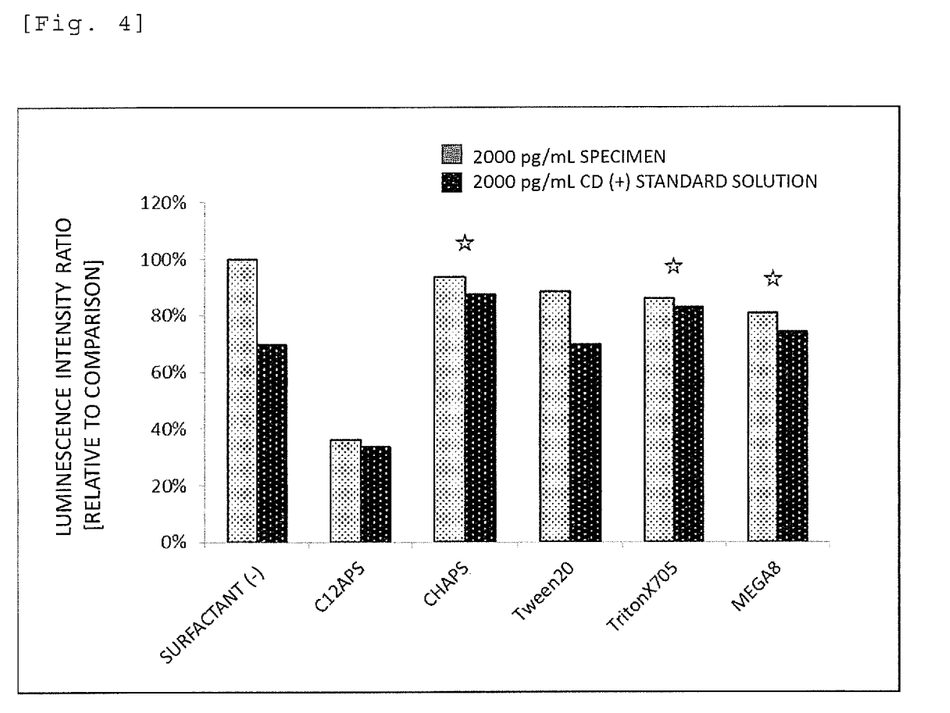
FIG. 4 is a graph illustrating the exclusion effect of various surfactants on aldosterone included in HPβCD. Measurement was performed by a non-competitive method (two-step method) using a serum-based standard solution.

FIG. 4 illustrates the ratio of luminescence intensity when each treatment liquid was used and the 2000 pg/mL CD (+) standard solution or 2000 pg/mL specimen was used as the sample (luminescence intensity ratio [relative to comparison]), where the luminescence intensity in the case of using, as the treatment liquid, the treatment liquid not added with a surfactant (surfactant (−)) and using, as the sample, the 2000 pg/mL specimen was set to 100% (comparison). As a result, it was found that the surfactants having an exclusion effect (effect of increasing the reactivity of the 2000 pg/mL CD (+) standard solution without changing the reactivity of the 2000 pg/mL specimen) were CHAPS, Triton X705, and MEGA8 (star marks in FIG. 4). This has revealed that a serum-based standard solution also gives results similar to those in the buffer solution-based standard solution illustrated in Example 1-3.

(Example 2) Effect of Excluding Progesterone from HPβCD

As in the case of aldosterone, it has been confirmed that progesterone also promotes exclusion from HPβCD by specific types of surfactants.

In the present example, the one-step competitive method was employed as the measurement system. In the competitive method in contrast to the two-step method (non-competitive method) of Examples 1-1 to 1-4, when the action of surfactant promotes the exclusion of steroid from HPβCD, the labeled antibody can no longer bind to the antigen-binding particles, which further reduces the luminescence intensity.

Specifically, progesterone was used as the antigen, and a buffer solution-based one was used as the standard solution. First, the following standard solution diluent (having same composition as the standard solution diluent of Example 1-3) was used to prepare a 20 ng/mL progesterone solution added with 20 ng/mL progesterone (standard solution) and a control solution not added with progesterone. The standard solution diluent used were "50 mM MOPS (pH 7.2), 150 mM NaCl, 1% HPβCD, 0.1% NaN$_3$."

Under the conditions of using no separate treatment liquid but using a surfactant, each of the following surfactants was added to the enzyme-labeled antibody below to a concentration of 0.2%. The surfactants used were, among the ones used in Example 1-3, Tween 20, Tween 80, C8APS, CHAPS, MEGA8, Triton X705, and sodium deoxycholate, as well as Brij58 (manufactured by ICI) and C16APS (manufactured by Tokyo Chemical Industry Co., Ltd.).

Measurement was carried out for each sample (each standard solution (20 ng/mL progesterone) and each control solution (0 ng/mL progesterone)) by the delay one-step method using an alkaline phosphatase-labeled anti-progesterone antibody (alkaline phosphatase-labeled anti-progesterone antibody (enzyme-labeled antibody) prepared by the conventional method) and progesterone-binding particles (progesterone-binding magnetic particles (antigen-binding particles) prepared by the conventional method). Specifically, the following steps (a) to (e) were carried out.

(a) About 10 μL of the sample is added to about 50 μL of enzyme-labeled antibody, and the mixture is stirred and reacted at 37° C. for 11 minutes (first reaction).
(b) About 50 μL of antigen-binding particles is added, and the mixture is stirred and reacted at 37° C. for 8 minutes (second reaction).
(c) B/F separation is carried out using a magnetic separator, followed by washing.
(d) About 200 μL of AMPPD (substrate, 3-(2'-spiroadamantane)-4-methoxy-4-(3"-phosphoryloxy) phenyl-1,2-dioxetane.disodium salt) is added, and the mixture is stirred and reacted at 37° C. for 4 minutes (enzymatic reaction).
(e) The luminescence intensity of light having a maximum emission peak in the vicinity of a wavelength of 463 nm, which is emitted with the decomposition of the substrate, is measured.

Figure 5:
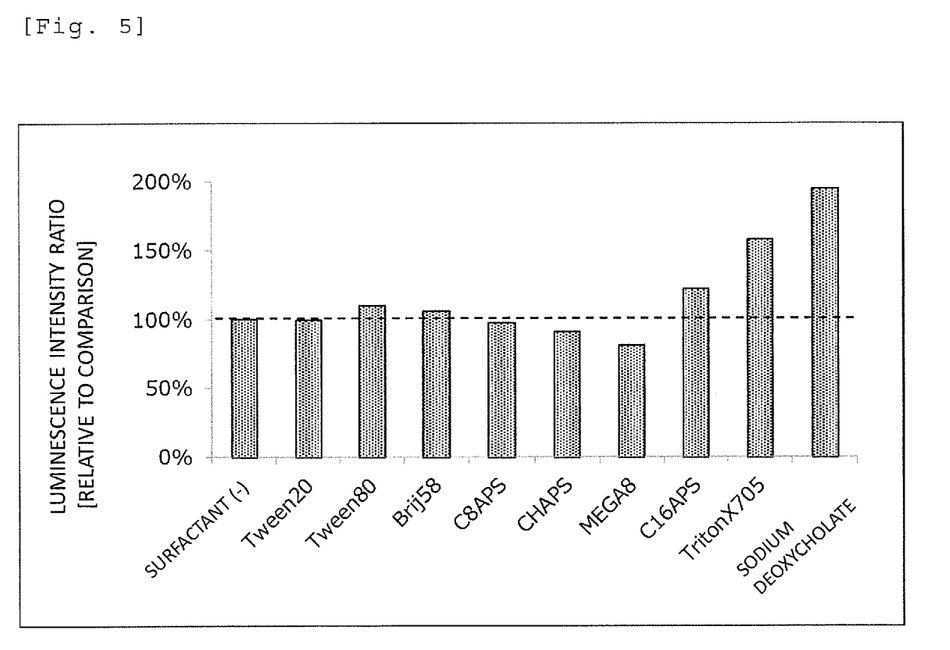
FIG. 5 is a graph illustrating the exclusion effect of various surfactants on progesterone included in HPβCD. Measurement was performed by a competitive method (one-step method) using a buffer solution-based standard solution.

FIG. 5 illustrates the ratio of the luminescence intensity when using the standard solution and the luminescence intensity when using the control solution under the conditions of using various surfactants (luminescence intensity ratio [relative to comparison]), where the ratio of the luminescence intensity when using the standard solution and the luminescence intensity when using the control solution under the condition of using no surfactant (surfactant (−)) (standard solution/control solution; comparison) was set to 100%. As a result, the luminescence intensity was particularly reduced for MEGA8 and CHAPS, from which the effect of excluding steroid from HPβCD in the one-step competitive method was confirmed. In particular, the effect of MEGA8 was high (FIG. 5). Note that it was suggested that Triton X705 and sodium deoxycholate adversely affected the reaction system itself. The surfactants effective in the progesterone measurement system were common to those effective in the aldosterone measurement system (Examples 1-3 and 1-4).

(Example 3) Effect of Excluding 25-Hydroxyvitamin D from γCD

In the present example, 25-hydroxyvitamin D was used as the antigen, a buffer solution-based one was used as the standard solution, and γCD was used as cyclodextrin. Specifically, first, 25-hydroxyvitamin D was added to the following standard solution diluent (without γCD) to prepare an approximately 50 ng/mL 25-hydroxyvitamin D solution (50 ng/mL CD (−) standard solution). Meanwhile, γCD was added to the standard solution diluent to a concentration of 0.3%, and 25-hydroxyvitamin D was added thereto to prepare an approximately 50 ng/mL 25-hydroxyvitamin D solution (50 ng/mL CD (+) standard solution). The standard solution diluents (without γCD) used were "50 mM MOPS (pH 7.2), 150 mM NaCl, 0.1% NaN$_3$."

In addition, the following treatment liquid base composition was used to prepare treatment liquids each of which was added or not added with 8 types among the surfactants used in Example 1 (Tween 80, Brij58, C8APS, C16APS, CHAPS, MEGA8, Triton X705, sodium deoxycholate). The treatment liquid base compositions were "50 mM Tris-HCl (pH 7.2), 150 mM NaCl, 4.5% BSA, 0.1% NaN$_3$." The concentration of the surfactant in each treatment liquid was 0.5%.

Measurement was carried out for each sample (50 ng/mL CD (−) standard solution or 50 ng/mL CD (+) standard solution) by the special two-step method using an anti-25-hydroxyvitamin D antibody-binding particles (anti-25-hydroxyvitamin D antibody-binding magnetic particles (antibody-binding particles) prepared by the conventional method), an alkaline phosphatase-labeled anti-25-hydroxyvitamin D immunocomplex antibody (alkaline phosphatase-labeled anti-25-hydroxyvitamin D antibody (enzyme-labeled antibody) prepared by the conventional method), and the above treatment liquids. Specifically, the following steps (a) to (g) were carried out.

(a) About 10 μL of the sample and about 190 μL of the treatment liquid are mixed to obtain a diluted sample diluted 20 times (pretreatment/dilution).
(b) About 20 μL of the diluted sample is added to about 50 μL of the antibody-binding particles, and the mixture is stirred and reacted at 37° C. for 8 minutes (first reaction).
(c) B/F separation is carried out using a magnetic separator, followed by washing.
(d) About 50 μL of enzyme-labeled antibody is added, and the mixture is stirred and reacted at 37° C. for 8 minutes (second reaction).
(e) B/F separation is carried out using a magnetic separator, followed by washing.
(f) About 200 μL of AMPPD (substrate, 3-(2'-spiroadamantane)-4-methoxy-4-(3"-phosphoryloxy) phenyl-1,2-dioxetane.disodium salt) solution is added, and the mixture is stirred and reacted at 37° C. for 4 minutes (enzymatic reaction).
(g) The luminescence intensity of light having a maximum emission peak in the vicinity of a wavelength of 463 nm, which is emitted with the decomposition of the substrate, is measured.

Figure 6:
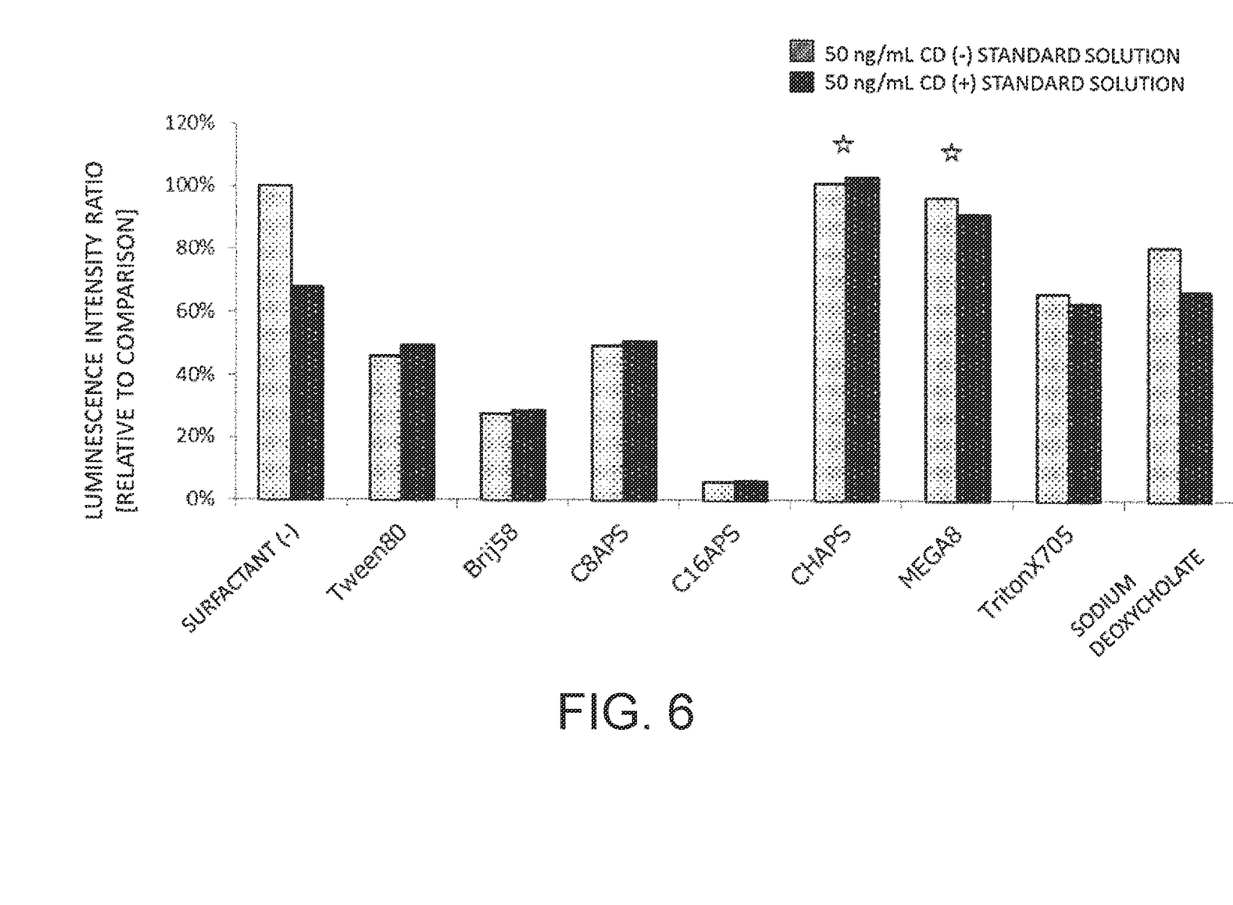
FIG. 6 is a graph illustrating the exclusion effect of various surfactants on 25-hydroxyvitamin D included in γCD. Measurement was performed by a non-competitive method (two-step method) using a buffer solution-based standard solution.

FIG. 6 illustrates the ratio of luminescence intensity when each treatment liquid was used and the 50 ng/mL CD (−) standard solution or 50 ng/mL CD (+) standard solution was used as the sample (luminescence intensity ratio [relative to comparison]), where the luminescence intensity in the case of using, as the treatment liquid, the treatment liquid not added with a surfactant (surfactant (−)) and using, as the sample, the 50 ng/mL CD (−) standard solution was set to 100% (comparison). As a result, CHAPS and MEGA8 was confirmed to particularly exhibit an exclusion effect (effect of increasing the luminescence intensity (reactivity) of 50 ng/mL CD (+) standard solution and suppressing the deviation from the luminescence intensity of 50 ng/mL CD (−)

standard solution) (star marks in FIG. 6). On the other hand, Brij58, C8APS, and C16APS were confirmed to suppress the deviation in luminescence intensity between the 50 ng/mL CD (−) standard solution and the 50 ng/mL CD (+) standard solution, but were suggested to adversely affect the reaction system itself, inhibiting the primary reaction to reduce the luminescence intensity.

(Example 4) Effect of Excluding Estradiol from HPβCD

In the present example, another method of the one-step competitive method of Example 2 was employed as the measurement system. In the competitive method, when the action of surfactant promotes the exclusion of steroid from HPβCD, and the amount itself of steroid in the sample increases relative to the amount of labeled antigen, the labeled antigen can no longer bind to the antibody-binding particles, which further reduces the luminescence intensity.

Specifically, estradiol (E2) was used as the antigen, a buffer solution-based one was used as the standard solution, and HPβCD was used as cyclodextrin. Specifically, first, the following standard solution diluent (without HPβCD) was used as a "0 pg/mL CD (−) standard solution (control)," and estradiol was added thereto to prepare an approximately 50 pg/mL estradiol solution (50 pg/mL CD (−) standard solution). Meanwhile, the above standard solution diluent added with HPβCD to a concentration of 0.2% was used as a "0 pg/mL CD (+) standard solution (control)," and estradiol was added thereto to prepare an approximately 50 pg/mL estradiol solution (50 pg/mL CD (+) standard solution). The standard solution diluents (without HPβCD) used were "50 mM Tris-HCl (pH 7.2), 150 mM NaCl, 5% BSA, 0.1% $NaN_3$."

In addition under the conditions of using no separate treatment liquid but using a surfactant, each of the following surfactants was added to the enzyme-labeled antigen below to a concentration of 1.0%. The surfactants used were, among were the ones used in Example 1, Tween 20, Tween 80, Brij58, C8APS, C16APS, CHAPS, MEGA8, and Triton X705.

Measurement was carried out for each sample (0 pg/mL CD (−) standard solution, 50 pg/mL CD (−) standard solution, 0 pg/mL CD (+) standard solution, 50 pg/mL CD (+) standard solution) by the one-step method using an anti-E2 antibody-binding particles (anti-E2 antibody-binding magnetic particles (antibody-binding particles) prepared by the conventional method) and an alkaline phosphatase-labeled E2 (alkaline phosphatase-labeled E2 (enzyme labeled antigen) prepared by the conventional method). Specifically, the following steps (a) to (d) were carried out.

(a) About 50 μL of the antibody-binding particles, about 20 μL of the sample, and about 50 μL of the enzyme labeled antigen are sequentially added, and the mixture is stirred and reacted at 37° C. for 19 minutes (first reaction).
(b) B/F separation is carried out using a magnetic separator, followed by washing.
(c) About 200 μL of AMPPD (substrate, 3-(2'-spiroadamantane)-4-methoxy-4-(3"-phosphoryloxy) phenyl-1,2-dioxetane.disodium salt) solution is added, and the mixture is stirred and reacted at 37° C. for 4 minutes (enzymatic reaction).
(d) The luminescence intensity of light having a maximum emission peak in the vicinity of a wavelength of 463 nm, which is emitted with the decomposition of the substrate, is measured.

Figure 7A:
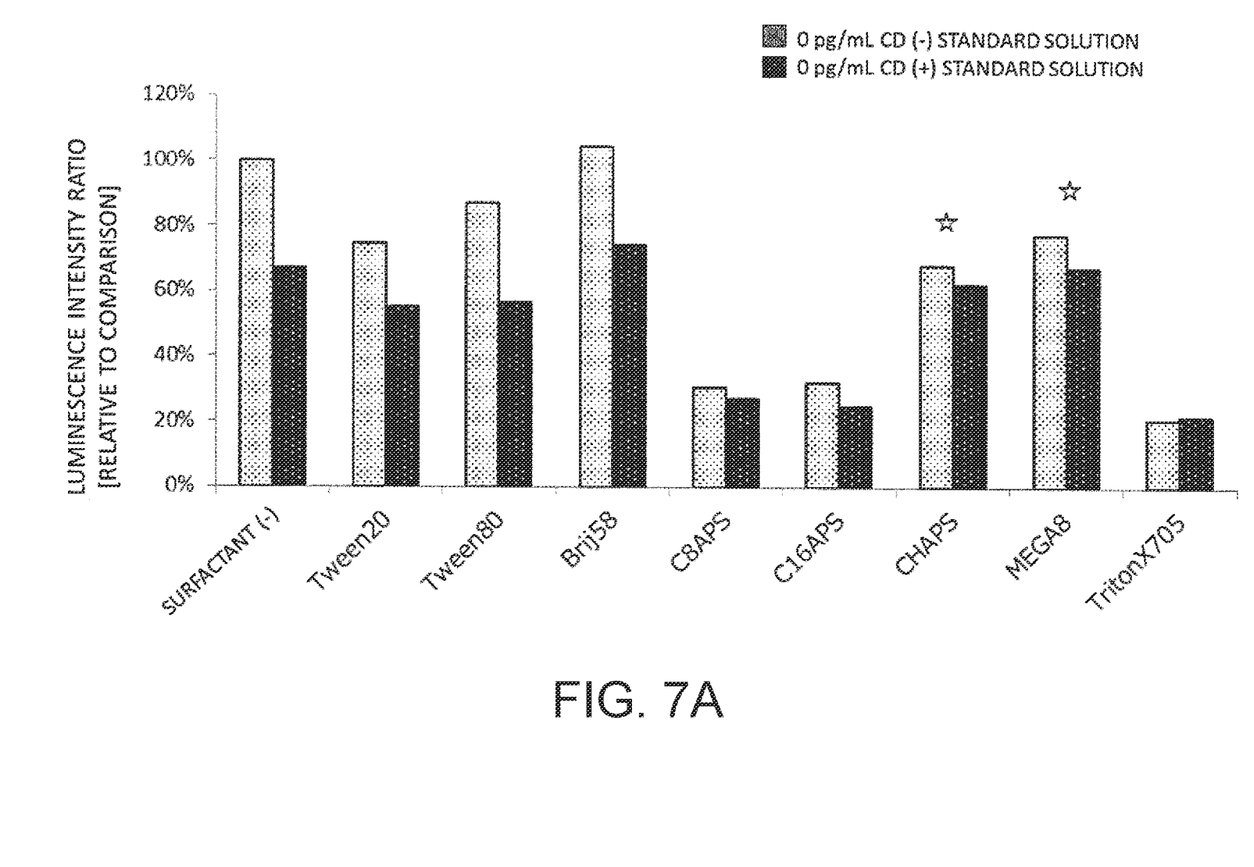
FIG. 7A is a graph illustrating the exclusion effect of various surfactants on estradiol included in HPβCD. Measurement was performed by a competitive method (one-step method) using a buffer solution-based standard solution.
Figure 7B:
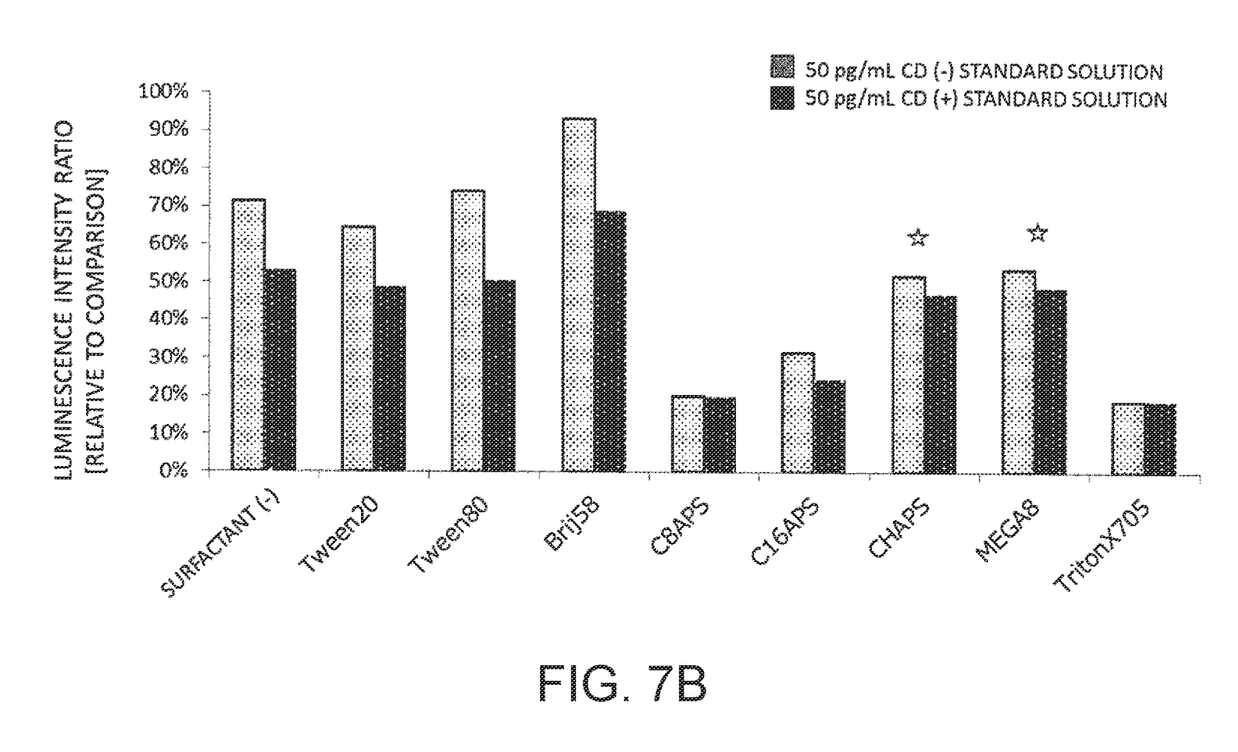
FIG. 7B is a graph illustrating the exclusion effect of various surfactants on estradiol included in HPβCD. Measurement was performed by a competitive method (one-step method) using a buffer solution-based standard solution.

FIG. 7A illustrates the ratio of the luminescence intensity when using the 0 pg/mL CD (−) standard solution or the 0 pg/mL CD (+) standard solution under the conditions of using or not using various surfactants (luminescence intensity ratio [relative to comparison]), where the ratio of the luminescence intensity when using the 0 pg/mL CD (−) standard solution under the condition of using no surfactant (surfactant (−)) (comparison) was set to 100%, and FIG. 7B illustrates the ratio of the luminescence intensity when using the 50 pg/mL CD (−) standard solution or the 50 pg/mL CD (+) standard solution under the conditions of using or not using surfactants (luminescence intensity ratio [relative to comparison]), where the ratio of the luminescence intensity when using the 50 pg/mL CD (−) standard solution under the condition of using no surfactant (surfactant (−)) (comparison) was set to 100%.

As a result, FIG. 7A and FIG. 7B are graphs having substantially the same outline. In addition, MEGA8 and CHAPS suppressed the reduction in the luminescence intensity under the condition of using no surfactant, and also suppressed the deviation in the luminescence intensity between the presence of addition (CD (+)) and the absence of addition (CD (−)) of cyclodextrin. Thus, the effect of excluding steroid from HPβCD was confirmed (star marks in FIG. 7A and FIG. 7B). In addition, C8APS and Triton X705 suppressed the deviation in the luminescence intensity between the presence of addition and the absence of addition of cyclodextrin, but were suggested to adversely affect the reaction system itself due to the addition of surfactant. The surfactants effective in the estradiol measurement system were common to those effective in the aldosterone measurement system (Examples 1-3 and 1-4), the progesterone measurement system (Example 2), and the 25-hydroxyvitamin D (Example 3).

INDUSTRIAL APPLICABILITY

As described above, the present invention makes it possible to suppress the deviation in behavior of the antigen-antibody reaction between the test sample and the standard solution, and quantify the concentration of a steroid in the test sample with high accuracy. Since steroid activity is associated with various diseases, the present invention is not limited to research use but can greatly contribute to the diagnosis of diseases.

The invention claimed is:
1. A method for immunologically quantifying a steroid, comprising:
   adding to a standard solution containing a target steroid and cyclodextrin, wherein the target steroid is included in the cyclodextrin and wherein the standard solution contains the target steroid at a predetermined concentration, a treatment liquid to exclude the target steroid from the cyclodextrin to form a standard solution treatment liquid mixture;
   reacting an anti-steroid antibody with each of a test sample containing the target steroid and the standard solution treatment liquid mixture to form antigen-antibody complexes in each of the test sample and the standard solution treatment liquid mixture;
   measuring a signal intensity of the antigen-antibody complexes in each of the test sample and the standard solution treatment liquid mixture, wherein the signal intensity of the antigen-antibody complexes measured in each of the test sample and the standard solution treatment liquid mixture is a luminescence intensity of light; and comparing the signal intensity of the test sample with the signal intensity of the standard solution treatment liquid mixture, to determine a concentration of the target steroid concentration in the test sample, wherein the treatment liquid comprises a surfactant as an active ingredient, and wherein the surfactant is at least one selected from the group consisting of N-octanoyl-N-methylglucamine and 3-[(3-cholamidopropyl)dimethylammonio]-1-propanesulfonate.

* * * * *